United States Patent
Ingimundarson et al.

(10) Patent No.: US 11,484,428 B2
(45) Date of Patent: Nov. 1, 2022

(54) PANEL ATTACHMENT AND CIRCUMFERENCE ADJUSTMENT SYSTEMS FOR AN ORTHOPEDIC DEVICE

(71) Applicant: Ossur HF, Reykjavik (IS)

(72) Inventors: Arni Thor Ingimundarson, Reykjavik (IS); Valgeir Petursson, Reykjavik (IS); Jeff Nemeth, Foothill Ranch, CA (US); Harry Duane Romo, Foothill Ranch, CA (US); Bjorn Omarsson, Reykjavik (IS); Steven Kamm, Foothill Ranch, CA (US)

(73) Assignee: OSSUR HF, Reykjavik (IS)

( * ) Notice: Subject to any disclaimer, the term of this patent is extended or adjusted under 35 U.S.C. 154(b) by 711 days.

(21) Appl. No.: 16/001,160

(22) Filed: Jun. 6, 2018

(65) Prior Publication Data
US 2018/0280183 A1 Oct. 4, 2018

Related U.S. Application Data

(63) Continuation of application No. 15/856,366, filed on Dec. 28, 2017, now Pat. No. 10,980,657, which is a
(Continued)

(51) Int. Cl.
*A61F 5/02* (2006.01)

(52) U.S. Cl.
CPC .................................. *A61F 5/028* (2013.01)

(58) Field of Classification Search
CPC .... A61F 5/055; A61F 5/05816; A61F 5/3707; A61F 5/012; A61F 5/05891;
(Continued)

(56) References Cited

U.S. PATENT DOCUMENTS

| 7,916 A | 1/1851 | Knapp |
| 61,487 A | 1/1867 | Vollschwitz |

(Continued)

FOREIGN PATENT DOCUMENTS

| AU | 20 1027 10 20 A1 | 2/2012 |
| AU | 20 1027 10 20 A2 | 2/2012 |

(Continued)

OTHER PUBLICATIONS

Pamphlet—"Bledsoe Phillippon K.A.F. Positioning Kit, Application Instructions (CP020205 Rev B Apr. 2007), New Hip Arthroscopy Padding and Positioning Kit", Council Directive 93142/EEC of Jun. 14, 1993 concerning Medical Devices, 2 pages.
(Continued)

*Primary Examiner* — Ophelia A Hawthorne
(74) *Attorney, Agent, or Firm* — Workman Nydegger

(57) ABSTRACT

A spinal orthosis includes posterior panels arranged with a flat spinal curvature to create a reverse three-point pressure system to the spine. The reverse three-point pressure system relieves pressure on the posterior side of the vertebrae beneficial for certain indications. Various arrangements allow for securing the posterior panel to the spinal orthosis. The spinal orthosis includes a belt member length adjustment system including belt members having end portions reducible in length and a belt panel adapted to secure to the end portion of the belt member reduced in length to form at least in part a belt circumference of the spinal orthosis.

10 Claims, 9 Drawing Sheets

Related U.S. Application Data continuation of application No. 14/031,092, filed on Sep. 19, 2013, now Pat. No. 9,872,794.

(60) Provisional application No. 61/702,906, filed on Sep. 19, 2012.

(58) Field of Classification Search
CPC ...... A61F 5/05883; A61F 5/024; A61F 5/026; A61F 13/12; A61F 2007/0009; A61F 5/00; A42B 3/0473; A47C 7/383
See application file for complete search history.

(56) References Cited

U.S. PATENT DOCUMENTS

| | | |
|---|---|---|
| 181,948 A | 9/1876 | Kleinschuster |
| 232,420 A | 9/1880 | Smith |
| 321,145 A | 6/1885 | Spencer |
| 321,146 A | 6/1885 | Spencer |
| 328,638 A | 10/1885 | Battershall |
| 368,699 A | 8/1887 | Zervas |
| 386,642 A | 7/1888 | Mann |
| 507,172 A | 10/1893 | Shelden |
| 571,749 A | 11/1896 | Colton |
| 596,849 A | 1/1898 | Combier |
| 601,446 A | 3/1898 | Mestler |
| 616,196 A | 12/1898 | Medbury |
| 629,900 A | 8/1899 | Fosburgh |
| 639,072 A | 12/1899 | Lyons |
| 664,250 A | 12/1900 | Fitzpatrick |
| 709,055 A | 9/1902 | Sheldon |
| 714,124 A | 11/1902 | Adams |
| 746,563 A | 12/1903 | McMahon |
| 772,926 A | 10/1904 | Colton |
| 787,894 A | 4/1905 | Colton |
| 888,490 A | 5/1908 | Haas |
| 894,066 A | 7/1908 | Scapra |
| 980,457 A | 1/1911 | Toles |
| 1,124,596 A | 1/1915 | Dalpe |
| 1,316,915 A | 9/1919 | Meyer et al. |
| 1,393,188 A | 10/1921 | Whiteman |
| 1,463,579 A | 7/1923 | Funck |
| 1,469,661 A | 10/1923 | Migita |
| 1,481,903 A | 1/1924 | Hart |
| 1,530,713 A | 3/1925 | Clark |
| 1,558,661 A | 10/1925 | Yeganian |
| 1,607,032 A | 11/1926 | Whitley |
| 1,755,641 A | 4/1930 | Foulke |
| 1,948,785 A | 2/1934 | Dondelinger |
| 1,981,157 A | 11/1934 | Walter |
| 2,036,484 A | 4/1936 | May |
| 2,100,964 A | 11/1937 | Kendrick |
| 2,117,309 A | 5/1938 | Fritsch |
| 2,219,475 A | 10/1940 | Flaherty |
| 2,409,381 A | 10/1946 | Pease, Jr. |
| 2,543,370 A | 2/1951 | Kludt et al. |
| 2,554,337 A | 5/1951 | Lampert |
| 2,630,801 A | 3/1953 | Mest et al. |
| 2,696,011 A | 12/1954 | Galdik |
| 2,749,550 A | 6/1956 | Pease |
| 2,775,767 A | 1/1957 | Gould |
| 2,793,368 A | 5/1957 | Nouel |
| 2,808,050 A | 10/1957 | Ward |
| 2,815,021 A | 12/1957 | Freeman |
| 2,828,737 A | 4/1958 | Hale |
| 2,904,040 A | 9/1959 | Hale |
| 2,906,260 A | 9/1959 | Myers |
| 2,906,261 A | 9/1959 | Craig |
| 3,095,875 A | 7/1963 | Davidson et al. |
| 3,096,760 A | 7/1963 | Nelkin |
| 3,128,514 A | 4/1964 | Parker et al. |
| 3,274,996 A | 9/1966 | Jewett |
| 3,282,264 A | 11/1966 | Connelly |
| 3,351,053 A | 11/1967 | Stuttle |
| 3,371,351 A | 3/1968 | Allain |
| 3,434,469 A | 3/1969 | Swift |
| 3,480,012 A | 11/1969 | Smithers et al. |
| 3,509,875 A | 5/1970 | Richter |
| 3,548,817 A | 12/1970 | Mittasch |
| 3,563,431 A | 2/1971 | Pletz |
| 3,570,480 A | 3/1971 | Stubbs |
| 3,578,773 A | 5/1971 | Schultz |
| 3,600,717 A | 8/1971 | McKeehan |
| 3,601,819 A | 8/1971 | Herrmann |
| 3,603,316 A | 9/1971 | Lehman |
| 3,762,421 A | 10/1973 | Sax, Sr. |
| 3,771,513 A | 11/1973 | Velazquez |
| 3,793,749 A | 2/1974 | Gertsch et al. |
| 3,808,644 A | 5/1974 | Schoch |
| 3,812,850 A | 5/1974 | Reiman |
| 3,816,211 A | 6/1974 | Haigh |
| 3,834,048 A | 9/1974 | Maurer |
| 3,889,664 A | 6/1975 | Heuser et al. |
| 3,902,503 A | 9/1975 | Gaylord, Jr. |
| 3,920,008 A | 11/1975 | Lehman |
| 3,926,182 A | 12/1975 | Stabholz |
| 3,927,665 A | 12/1975 | Wax |
| 3,945,376 A | 3/1976 | Kuehnegger |
| 4,042,433 A | 8/1977 | Hardy et al. |
| 4,055,168 A | 10/1977 | Miller et al. |
| 4,071,387 A | 1/1978 | Schlaepfer |
| 4,099,524 A | 7/1978 | Cueman et al. |
| 4,114,788 A | 9/1978 | Zurich |
| 4,162,672 A | 7/1979 | Yazaki |
| 4,173,973 A | 11/1979 | Hendricks |
| 4,175,553 A | 11/1979 | Rosenberg |
| 4,182,338 A | 1/1980 | Stanulis |
| 4,230,101 A | 10/1980 | Gold |
| 4,261,081 A | 4/1981 | Lott |
| 4,285,336 A | 8/1981 | Oebser et al. |
| 4,308,861 A | 1/1982 | Kelly |
| 4,322,092 A | 3/1982 | Feucht et al. |
| 4,383,523 A | 5/1983 | Schurman |
| 4,392,489 A | 7/1983 | Wagner, Sr. |
| 4,433,456 A | 2/1984 | Baggio |
| RE31,564 E | 4/1984 | Hendricks |
| 4,475,543 A | 10/1984 | Brooks et al. |
| 4,479,495 A | 10/1984 | Isaacson |
| 4,494,536 A | 1/1985 | Latenser |
| 4,502,471 A | 3/1985 | Owens |
| 4,508,110 A | 4/1985 | Modglin |
| 4,531,515 A | 7/1985 | Rolfes |
| 4,555,830 A | 12/1985 | Petrini et al. |
| 4,559,933 A | 12/1985 | Batard et al. |
| 4,569,336 A | 2/1986 | Wheeler |
| 4,574,500 A | 3/1986 | Aldinio et al. |
| 4,574,789 A | 3/1986 | Forster |
| 4,574,790 A | 3/1986 | Wellershaus |
| 4,590,939 A | 5/1986 | Sakowski |
| 4,608,971 A | 9/1986 | Borschneck |
| 4,616,524 A | 10/1986 | Bidoia |
| 4,619,657 A | 10/1986 | Keates et al. |
| 4,628,913 A | 12/1986 | Lerman |
| 4,631,839 A | 12/1986 | Bonetti et al. |
| 4,631,840 A | 12/1986 | Gamm |
| 4,635,626 A | 1/1987 | Lerman |
| 4,640,269 A | 2/1987 | Goins |
| 4,648,390 A | 3/1987 | Friddle |
| 4,649,574 A | 3/1987 | Michels |
| 4,654,985 A | 4/1987 | Chalmers |
| 4,655,201 A | 4/1987 | Pirmantgen |
| 4,658,807 A | 4/1987 | Swain |
| 4,660,302 A | 4/1987 | Arieh et al. |
| 4,677,699 A | 7/1987 | Barabe |
| 4,677,969 A | 7/1987 | Calabrese |
| 4,680,878 A | 7/1987 | Pozzobon et al. |
| 4,691,696 A | 9/1987 | Farfan De Los Godos |
| 4,696,291 A | 9/1987 | Tyo |
| 4,697,583 A | 10/1987 | Mason et al. |
| 4,697,592 A | 10/1987 | Maddux et al. |
| 4,716,898 A | 1/1988 | Chauve et al. |
| 4,719,670 A | 1/1988 | Kurt |
| 4,719,709 A | 1/1988 | Vaccari |
| 4,761,834 A | 8/1988 | Kolb |

(56) References Cited

U.S. PATENT DOCUMENTS

| | | |
|---|---|---|
| 4,796,610 A | 1/1989 | Cromartie |
| 4,799,297 A | 1/1989 | Baggio et al. |
| 4,802,291 A | 2/1989 | Sartor |
| 4,805,605 A | 2/1989 | Glassman |
| 4,807,605 A | 2/1989 | Mattingly |
| 4,811,503 A | 3/1989 | Iwama |
| 4,843,688 A | 7/1989 | Ikeda |
| 4,862,878 A | 9/1989 | Davison et al. |
| 4,870,761 A | 10/1989 | Tracy |
| 4,905,678 A | 3/1990 | Cumins et al. |
| 4,923,474 A | 5/1990 | Klasson et al. |
| 4,937,952 A | 7/1990 | Olivieri |
| 4,961,544 A | 10/1990 | Bidoia |
| 4,963,208 A | 10/1990 | Muncy et al. |
| 4,976,257 A | 12/1990 | Akin et al. |
| 4,986,263 A | 1/1991 | Dickerson et al. |
| 4,997,438 A | 3/1991 | Nipper |
| 5,027,482 A | 7/1991 | Torppey |
| 5,072,725 A | 12/1991 | Miller |
| 5,074,288 A | 12/1991 | Miller |
| 5,092,321 A | 3/1992 | Spademan |
| 5,098,770 A | 3/1992 | Paire |
| 5,105,828 A | 4/1992 | Grant |
| 5,111,807 A | 5/1992 | Spahn et al. |
| 5,117,567 A | 6/1992 | Berger |
| 5,120,288 A | 6/1992 | Sinaki |
| 5,121,741 A | 6/1992 | Bremer et al. |
| 5,127,897 A | 7/1992 | Roller |
| 5,135,470 A | 8/1992 | Reeves |
| 5,135,471 A | 8/1992 | Houswerth |
| 5,154,690 A | 10/1992 | Shiono |
| 5,157,813 A | 10/1992 | Carroll |
| 5,170,505 A | 12/1992 | Rohrer |
| 5,171,296 A | 12/1992 | Herman |
| 5,176,131 A | 1/1993 | Votel et al. |
| 5,177,882 A | 1/1993 | Berger |
| 5,181,331 A | 1/1993 | Berger |
| 5,183,036 A | 2/1993 | Spademan |
| D334,063 S | 3/1993 | Dewall |
| 5,199,940 A | 4/1993 | Morris et al. |
| 5,201,074 A | 4/1993 | Dicker |
| 5,203,765 A | 4/1993 | Friddle, Jr. |
| 5,215,518 A | 6/1993 | Rosen |
| 5,226,874 A | 7/1993 | Heinz et al. |
| 5,230,698 A | 7/1993 | Garth |
| 5,259,831 A | 11/1993 | Lebron |
| 5,259,833 A | 11/1993 | Barnett |
| 5,267,928 A | 12/1993 | Barile et al. |
| 5,295,947 A | 3/1994 | Muncy |
| 5,295,996 A | 3/1994 | Blair |
| 5,307,521 A | 5/1994 | Davis |
| 5,313,952 A | 5/1994 | Hoch |
| 5,318,575 A | 6/1994 | Chesterfield et al. |
| 5,327,662 A | 7/1994 | Hallenbeck |
| 5,334,135 A | 8/1994 | Grim et al. |
| 5,342,289 A | 8/1994 | Munny |
| 5,346,461 A | 9/1994 | Heinz et al. |
| 5,363,863 A | 11/1994 | Lelli et al. |
| 5,365,947 A | 11/1994 | Bonutti |
| 5,368,552 A | 11/1994 | Williamson et al. |
| 5,376,129 A | 12/1994 | Faulkner et al. |
| 5,383,893 A | 1/1995 | Daneshvar |
| 5,387,245 A | 2/1995 | Fay et al. |
| 5,399,151 A | 3/1995 | Smith |
| 5,421,809 A | 6/1995 | Rise |
| 5,423,852 A | 6/1995 | Daneshvar |
| 5,429,587 A | 7/1995 | Gates |
| 5,433,648 A | 7/1995 | Frydman |
| 5,433,697 A | 7/1995 | Cox |
| 5,435,015 A | 7/1995 | Ellis-Brewer |
| 5,437,614 A | 8/1995 | Grim |
| 5,437,617 A | 8/1995 | Heinz et al. |
| 5,437,619 A | 8/1995 | Malewicz et al. |
| 5,449,338 A | 9/1995 | Trudell |
| 5,450,858 A | 9/1995 | Zablotsky et al. |
| 5,466,214 A | 11/1995 | Calderon-Garciduenas |
| 5,484,395 A | 1/1996 | Deroche |
| 5,499,965 A | 3/1996 | Sanchez |
| 5,500,959 A | 3/1996 | Yewer, Jr. |
| 5,502,902 A | 4/1996 | Sussmann |
| 5,503,314 A | 4/1996 | Fiscus |
| 5,503,620 A | 4/1996 | Danzger |
| 5,507,681 A | 4/1996 | Smith et al. |
| 5,507,834 A | 4/1996 | Laghi |
| 5,520,619 A | 5/1996 | Martin |
| 5,522,792 A | 6/1996 | Bassett et al. |
| 5,531,669 A | 7/1996 | Varnau |
| 5,536,246 A | 7/1996 | Saunders |
| 5,539,020 A | 7/1996 | Bracken et al. |
| 5,548,843 A | 8/1996 | Chase et al. |
| 5,551,950 A | 9/1996 | Oppen |
| 5,556,374 A | 9/1996 | Grace et al. |
| 5,558,628 A | 9/1996 | Bzoch |
| 5,569,171 A | 10/1996 | Muncy |
| 5,571,355 A | 11/1996 | Kornylo |
| 5,599,287 A | 2/1997 | Beczak, Sr. et al. |
| 5,599,288 A | 2/1997 | Shirley et al. |
| 5,603,122 A | 2/1997 | Kania |
| 5,620,412 A | 4/1997 | Modglin |
| 5,622,529 A | 4/1997 | Calabrese |
| 5,632,724 A | 5/1997 | Lerman et al. |
| 5,634,891 A | 6/1997 | Beczak, Sr. et al. |
| 5,638,588 A | 6/1997 | Jungkind |
| 5,669,116 A | 9/1997 | Jungkind |
| 5,674,187 A | 10/1997 | Zepf |
| 5,681,270 A | 10/1997 | Klearman et al. |
| 5,685,830 A | 11/1997 | Bonutti |
| 5,685,831 A | 11/1997 | Floyd |
| 5,688,137 A | 11/1997 | Bustance |
| 5,690,260 A | 11/1997 | Mkins et al. |
| 5,690,609 A * | 11/1997 | Heinze, III ............ A61F 5/028 128/115.1 |
| 5,695,452 A | 12/1997 | Grim et al. |
| 5,695,520 A | 12/1997 | Bruckner et al. |
| 5,704,904 A | 1/1998 | Dunfee |
| 5,704,937 A | 1/1998 | Martin |
| 5,708,977 A | 1/1998 | Morkunas |
| 5,718,670 A | 2/1998 | Bremer |
| 5,722,940 A | 3/1998 | Gaylord, Jr. et al. |
| 5,724,993 A | 3/1998 | Dunfee |
| 5,725,139 A | 3/1998 | Smith |
| 5,728,054 A | 3/1998 | Martin |
| 5,728,168 A | 3/1998 | Laghi et al. |
| 5,732,483 A | 3/1998 | Cagliari |
| 5,735,807 A | 4/1998 | Cropper |
| 5,737,854 A | 4/1998 | Sussmann |
| 5,746,218 A | 5/1998 | Edge |
| 5,752,640 A | 5/1998 | Proulx |
| 5,778,565 A | 7/1998 | Holt et al. |
| 5,782,782 A | 7/1998 | Miller |
| 5,795,316 A | 8/1998 | Gaylord |
| RE35,940 E | 10/1998 | Heinz et al. |
| 5,816,251 A | 10/1998 | Glisan |
| 5,819,378 A | 10/1998 | Doyle |
| 5,823,981 A | 10/1998 | Grim et al. |
| 5,826,766 A | 10/1998 | Aftanas |
| 5,827,211 A | 10/1998 | Sellinger |
| 5,830,167 A | 11/1998 | Jung |
| 5,836,493 A | 11/1998 | Grunsted et al. |
| 5,840,050 A | 11/1998 | Lerman |
| 5,840,051 A | 11/1998 | Towsley |
| 5,848,979 A | 12/1998 | Bonutti et al. |
| 5,853,378 A | 12/1998 | Modglin |
| 5,853,379 A | 12/1998 | Ostojic |
| 5,857,988 A | 1/1999 | Shirley |
| 5,868,292 A | 2/1999 | Stephens et al. |
| 5,890,640 A | 4/1999 | Thompson |
| 5,891,061 A | 4/1999 | Kaiser |
| 5,893,871 A | 4/1999 | Tanaka |
| 5,911,697 A | 6/1999 | Biedermann et al. |
| 5,916,070 A | 6/1999 | Donohue |
| 5,938,629 A | 8/1999 | Bloedau |
| 5,950,628 A | 9/1999 | Dunfee |
| 5,954,250 A | 9/1999 | Hall et al. |

(56) References Cited

U.S. PATENT DOCUMENTS

| | | |
|---|---|---|
| 5,954,253 A | 9/1999 | Swetish |
| 5,967,998 A | 10/1999 | Modglin |
| 5,968,002 A | 10/1999 | Morrisseau |
| 5,993,403 A | 11/1999 | Martin |
| 6,007,503 A | 12/1999 | Berger et al. |
| 6,010,472 A | 1/2000 | Schiller |
| 6,027,466 A | 2/2000 | Diefenbacher et al. |
| 6,029,273 A | 2/2000 | McCrane |
| 6,036,664 A | 3/2000 | Martin, Sr. et al. |
| 6,039,707 A | 3/2000 | Crawford et al. |
| 6,063,047 A | 5/2000 | Minne |
| 6,066,108 A | 5/2000 | Lundberg |
| 6,070,776 A | 6/2000 | Furnary et al. |
| 6,090,057 A | 7/2000 | Collins et al. |
| 6,099,490 A * | 8/2000 | Turtzo .................. A61F 5/028 2/311 |
| 6,110,138 A | 8/2000 | Shirley |
| 6,117,096 A | 9/2000 | Hassard |
| RE36,905 E | 10/2000 | Noble et al. |
| 6,125,792 A | 10/2000 | Gee |
| 6,129,638 A | 10/2000 | Davis |
| 6,129,691 A | 10/2000 | Ruppert |
| 6,156,001 A | 12/2000 | Frangi et al. |
| 6,159,248 A | 12/2000 | Gramnas |
| 6,182,288 B1 | 2/2001 | Kibbee |
| 6,189,538 B1 | 2/2001 | Thorpe |
| 6,190,343 B1 | 2/2001 | Heinz et al. |
| D438,624 S | 3/2001 | Reina |
| 6,206,932 B1 | 3/2001 | Johnson |
| 6,213,968 B1 | 4/2001 | Heinz et al. |
| 6,227,937 B1 | 5/2001 | Principe |
| 6,245,033 B1 | 6/2001 | Martin |
| 6,254,561 B1 | 7/2001 | Borden |
| 6,256,798 B1 | 7/2001 | Egolf et al. |
| 6,267,390 B1 | 7/2001 | Maravetz et al. |
| 6,282,729 B1 | 9/2001 | Oikawa et al. |
| 6,289,558 B1 | 9/2001 | Hammerslag |
| 6,315,746 B1 | 11/2001 | Garth et al. |
| 6,322,529 B1 | 11/2001 | Chung |
| 6,325,023 B1 | 12/2001 | Elnatan |
| 6,338,723 B1 | 1/2002 | Carpenter et al. |
| 6,375,632 B1 | 4/2002 | Albrecht et al. |
| 6,401,786 B1 | 6/2002 | Tedeschi et al. |
| 6,413,232 B1 | 7/2002 | Townsend et al. |
| 6,416,074 B1 | 7/2002 | Maravetz et al. |
| 6,419,652 B1 | 7/2002 | Slautterback |
| 6,425,876 B1 | 7/2002 | Frangi et al. |
| 6,428,493 B1 | 8/2002 | Pior et al. |
| 6,432,073 B2 | 8/2002 | Pior et al. |
| 6,471,665 B1 | 10/2002 | Milbourn et al. |
| 6,478,759 B1 | 11/2002 | Modglin et al. |
| 6,494,853 B1 | 12/2002 | Rossi et al. |
| 6,502,577 B1 | 1/2003 | Bonutti |
| 6,503,213 B2 | 1/2003 | Bonutti |
| 6,517,502 B2 | 2/2003 | Heyman et al. |
| 6,540,703 B1 | 4/2003 | Lerman |
| 6,589,195 B1 | 7/2003 | Schwenn et al. |
| 6,602,214 B2 | 8/2003 | Heinz et al. |
| 6,605,052 B1 | 8/2003 | Cool et al. |
| 6,609,642 B2 | 8/2003 | Heinz et al. |
| 6,623,419 B1 | 9/2003 | Smith et al. |
| 6,652,596 B2 | 11/2003 | Smith et al. |
| 6,656,144 B1 | 12/2003 | Coligado |
| 6,676,617 B1 | 1/2004 | Miller |
| 6,676,620 B2 | 1/2004 | Schwenn et al. |
| 6,688,943 B2 | 2/2004 | Nagaoka |
| 6,689,080 B2 | 2/2004 | Castillo |
| 6,702,770 B2 | 3/2004 | Bremer et al. |
| 6,711,750 B1 | 3/2004 | Yoo |
| 6,711,787 B2 | 3/2004 | Jungkind et al. |
| 6,726,643 B1 | 4/2004 | Martin |
| 6,769,155 B2 | 8/2004 | Hess et al. |
| 6,770,047 B2 | 8/2004 | Bonutti |
| 6,773,411 B1 | 8/2004 | Alvarez |
| 6,790,191 B1 | 9/2004 | Hendricks |
| 6,802,442 B1 | 10/2004 | Thompson |
| D499,806 S | 12/2004 | Machin et al. |
| 6,827,653 B2 | 12/2004 | Be |
| D501,078 S | 1/2005 | Cabana |
| 6,893,098 B2 | 5/2005 | Kohani |
| 6,893,411 B1 | 5/2005 | Modglin |
| 6,913,585 B2 | 7/2005 | Salmon et al. |
| 6,921,375 B2 | 7/2005 | Kihara |
| 6,921,377 B2 | 7/2005 | Bonutti |
| 6,923,780 B2 | 8/2005 | Price et al. |
| 6,926,685 B1 | 8/2005 | Modglin |
| 6,936,021 B1 | 8/2005 | Smith |
| 6,942,630 B2 | 9/2005 | Behan |
| 6,951,547 B1 | 10/2005 | Park et al. |
| 6,962,572 B1 | 11/2005 | Zahiri |
| 6,964,644 B1 | 11/2005 | Garth |
| 6,991,611 B2 | 1/2006 | Rhee |
| 7,001,348 B2 | 2/2006 | Garth et al. |
| 7,001,350 B2 | 2/2006 | Grosso |
| 7,025,737 B2 | 4/2006 | Modglin |
| 7,028,873 B1 | 4/2006 | Collier et al. |
| 7,034,251 B1 | 4/2006 | Child et al. |
| 7,048,707 B2 | 5/2006 | Schwenn et al. |
| 7,074,204 B2 | 7/2006 | Fujii et al. |
| 7,083,584 B2 | 8/2006 | Coligado |
| 7,083,585 B2 | 8/2006 | Latham |
| 7,087,032 B1 | 8/2006 | Ikeda |
| 7,101,348 B2 | 9/2006 | Garth et al. |
| 7,118,543 B2 | 10/2006 | Telles et al. |
| 7,128,724 B2 | 10/2006 | Marsh |
| 7,134,224 B2 | 11/2006 | Elkington et al. |
| 7,137,973 B2 | 11/2006 | Plauche et al. |
| 7,140,691 B2 | 11/2006 | Kohani |
| 7,166,083 B2 | 1/2007 | Bledsoe |
| 7,186,229 B2 | 3/2007 | Schwenn et al. |
| 7,198,610 B2 | 4/2007 | Ingimundarson et al. |
| 7,201,727 B2 | 4/2007 | Schwenn et al. |
| 7,235,059 B2 | 6/2007 | Mason et al. |
| 7,281,341 B2 | 10/2007 | Reagan et al. |
| 7,306,571 B2 | 12/2007 | Schwenn et al. |
| 7,306,573 B2 | 12/2007 | Bonutti |
| 7,309,304 B2 | 12/2007 | Stewart et al. |
| 7,316,660 B1 | 1/2008 | Modglin |
| 7,320,670 B1 | 1/2008 | Modglin |
| 7,322,950 B2 | 1/2008 | Modglin |
| 7,329,231 B2 | 2/2008 | Frank |
| 7,331,126 B2 | 2/2008 | Johnson |
| 7,351,368 B2 | 4/2008 | Abrams |
| 7,389,547 B1 | 6/2008 | Wiens |
| 7,402,147 B1 | 7/2008 | Allen |
| 7,404,804 B2 | 7/2008 | Bonutti |
| 7,416,565 B1 | 8/2008 | Al-Turaikl |
| 7,438,698 B2 | 10/2008 | Daiju |
| 7,473,235 B2 | 1/2009 | Schwenn et al. |
| 7,476,185 B2 | 1/2009 | Drennan |
| 7,513,018 B2 | 4/2009 | Koenig et al. |
| 7,549,970 B2 | 6/2009 | Tweardy |
| 7,578,798 B2 | 8/2009 | Rhee |
| 7,591,050 B2 | 9/2009 | Hammerslag |
| 7,597,671 B2 | 10/2009 | Baumgartner et al. |
| 7,597,672 B2 | 10/2009 | Kruijsen et al. |
| 7,600,660 B2 | 10/2009 | Kasper et al. |
| 7,615,021 B2 | 11/2009 | Nordt, III et al. |
| 7,618,386 B2 | 11/2009 | Nordt, III et al. |
| 7,618,389 B2 | 11/2009 | Nordt, III et al. |
| 7,654,972 B2 | 2/2010 | Alleyne |
| 7,662,121 B2 | 2/2010 | Zours |
| 7,670,306 B2 | 3/2010 | Nordt, III et al. |
| 7,682,219 B2 | 3/2010 | Falla |
| 7,699,797 B2 | 4/2010 | Nordt, III et al. |
| 7,704,219 B2 | 4/2010 | Nordt, III et al. |
| 7,727,048 B2 | 6/2010 | Gransberry |
| 7,727,174 B2 | 6/2010 | Chang et al. |
| 7,757,307 B2 | 7/2010 | Wong |
| 7,775,999 B2 | 8/2010 | Brown |
| 7,806,842 B2 | 10/2010 | Stevenson et al. |
| 7,815,585 B2 | 10/2010 | Vollbrecht |
| 7,819,831 B2 | 10/2010 | Dellanno |
| 7,833,182 B2 | 11/2010 | Hughes |

(56) References Cited

U.S. PATENT DOCUMENTS

| | | |
|---|---|---|
| 7,842,000 B2 | 11/2010 | Lai et al. |
| 7,857,776 B2 | 12/2010 | Frisbie |
| 7,862,529 B2 | 1/2011 | Brown |
| 7,862,621 B2 | 1/2011 | Kloos et al. |
| 7,871,388 B2 | 1/2011 | Brown |
| 7,878,998 B2 | 2/2011 | Nordt, III et al. |
| 7,887,500 B2 | 2/2011 | Nordt, III et al. |
| 7,914,473 B2 | 3/2011 | Josey |
| D636,494 S | 4/2011 | Garth et al. |
| 7,922,680 B2 | 4/2011 | Nordt, III et al. |
| 7,950,112 B2 | 5/2011 | Hammerslag et al. |
| 7,954,204 B2 | 6/2011 | Hammerslag et al. |
| 7,959,591 B2 | 6/2011 | Powers et al. |
| 3,006,877 A1 | 8/2011 | Lowry et al. |
| 7,993,296 B2 | 8/2011 | Nordt, III et al. |
| 8,002,724 B2 | 8/2011 | Hu et al. |
| 8,038,635 B2 | 10/2011 | Dellanno |
| 8,038,637 B2 | 10/2011 | Bonutti |
| 8,047,893 B2 | 11/2011 | Fenske |
| 8,048,014 B2 | 11/2011 | Brown |
| 8,066,161 B2 | 11/2011 | Green et al. |
| 8,066,654 B2 | 11/2011 | Sandifer et al. |
| 8,091,182 B2 | 1/2012 | Hammerslag et al. |
| 8,142,377 B2 | 3/2012 | Garth et al. |
| 8,162,194 B2 | 4/2012 | Gleason |
| 8,162,864 B2 | 4/2012 | Kruijsen et al. |
| 8,172,779 B2 | 5/2012 | Ingimundarson et al. |
| 8,214,926 B2 | 7/2012 | Brown |
| 8,216,167 B2 | 7/2012 | Garth et al. |
| 8,303,528 B2 | 11/2012 | Ingimundarson et al. |
| 8,308,669 B2 | 11/2012 | Nace |
| 8,308,670 B2 | 11/2012 | Sandifer et al. |
| 8,308,869 B2 | 11/2012 | Gardner et al. |
| 8,372,023 B2 | 2/2013 | Garth et al. |
| 8,381,314 B2 | 2/2013 | Takamoto et al. |
| 8,556,840 B2 | 10/2013 | Burke et al. |
| 8,597,222 B2 | 12/2013 | Lucero et al. |
| 8,657,769 B2 | 2/2014 | Ingimundarson et al. |
| 8,728,019 B2 | 5/2014 | Kruijsen et al. |
| 8,795,215 B2 | 8/2014 | Rossi |
| 8,893,312 B2 | 11/2014 | Takamoto et al. |
| 8,956,315 B2 | 2/2015 | Garth et al. |
| 9,370,440 B2 | 6/2016 | Ingimundarson et al. |
| 9,468,554 B2 | 10/2016 | Petursson et al. |
| 9,554,935 B2 | 1/2017 | Ingimundarson et al. |
| 9,572,705 B2 | 2/2017 | Ingimundarson et al. |
| 9,795,500 B2 | 10/2017 | Ingimundarson et al. |
| 2001/0020144 A1 | 9/2001 | Heinz et al. |
| 2001/0031936 A1 | 10/2001 | Pior et al. |
| 2002/0032397 A1 | 3/2002 | Coligado |
| 2002/0068890 A1 | 6/2002 | Schwenn et al. |
| 2002/0148461 A1 | 10/2002 | Heinz et al. |
| 2002/0158097 A1 | 10/2002 | Beale |
| 2003/0000986 A1 | 1/2003 | Smith |
| 2003/0028952 A1 | 2/2003 | Fujii et al. |
| 2003/0125650 A1 | 7/2003 | Grosso |
| 2003/0125705 A1 | 7/2003 | Ruman et al. |
| 2003/0139698 A1 | 7/2003 | Hyson |
| 2003/0220594 A1 | 11/2003 | Halvorson et al. |
| 2003/0229301 A1 | 12/2003 | Coligado |
| 2004/0024340 A1 | 2/2004 | Schwenn et al. |
| 2004/0050391 A1 | 3/2004 | Kiwala et al. |
| 2004/0082895 A1 | 4/2004 | Price et al. |
| 2004/0097857 A1 | 5/2004 | Reinecke et al. |
| 2004/0108350 A1 | 6/2004 | Warren |
| 2004/0116260 A1 | 6/2004 | Drennan |
| 2004/0132380 A1 | 7/2004 | Kihara |
| 2004/0133138 A1 | 7/2004 | Modglin |
| 2004/0143204 A1 | 7/2004 | Salmon et al. |
| 2004/0162582 A1 | 8/2004 | Banziger |
| 2004/0254505 A1 | 12/2004 | Begley et al. |
| 2005/0054960 A1 | 3/2005 | Telles et al. |
| 2005/0059917 A1 | 3/2005 | Garth et al. |
| 2005/0067816 A1 | 3/2005 | Buckman |
| 2005/0081339 A1 | 4/2005 | Sakabayashi |
| 2005/0131323 A1 | 6/2005 | Bledsoe |
| 2005/0137508 A1 | 6/2005 | Miller |
| 2005/0154337 A1 | 7/2005 | Meyer |
| 2005/0160627 A1 | 7/2005 | Dalgaard et al. |
| 2005/0165338 A1 | 7/2005 | Iglesias et al. |
| 2005/0228325 A1 | 10/2005 | Zours et al. |
| 2005/0240134 A1 | 10/2005 | Brown |
| 2005/0251074 A1* | 11/2005 | Latham ............ A61F 5/028 602/19 |
| 2005/0267390 A1 | 12/2005 | Garth et al. |
| 2005/0273025 A1 | 12/2005 | Houser |
| 2006/0011690 A1 | 1/2006 | Bareno |
| 2006/0052733 A1 | 3/2006 | Schwenn et al. |
| 2006/0064048 A1 | 3/2006 | Stano |
| 2006/0074365 A1 | 4/2006 | Brown |
| 2006/0079821 A1 | 4/2006 | Rauch |
| 2006/0129077 A1 | 6/2006 | Parizot |
| 2006/0135900 A1 | 6/2006 | Ingimundarson et al. |
| 2006/0135901 A1 | 6/2006 | Ingimundarson et al. |
| 2006/0135903 A1 | 6/2006 | Ingimundaron et al. |
| 2006/0155229 A1 | 7/2006 | Ceriani et al. |
| 2006/0156517 A1 | 7/2006 | Hammerslag et al. |
| 2006/0206992 A1 | 9/2006 | Godshaw et al. |
| 2006/0254598 A1 | 11/2006 | Saul |
| 2006/0260620 A1 | 11/2006 | Kazerooni et al. |
| 2007/0152007 A1 | 7/2007 | Kauss et al. |
| 2007/0167895 A1 | 7/2007 | Gramza et al. |
| 2007/0179417 A1 | 8/2007 | Schwenn et al. |
| 2007/0185425 A1 | 8/2007 | Einarsson et al. |
| 2008/0045873 A1 | 2/2008 | Zours |
| 2008/0091132 A1 | 4/2008 | Bonutti |
| 2008/0195010 A1 | 8/2008 | Lai et al. |
| 2008/0208090 A1 | 8/2008 | Vollbrecht |
| 2008/0208091 A1 | 8/2008 | Vollbrecht et al. |
| 2008/0249448 A1 | 10/2008 | Stevenson et al. |
| 2008/0262401 A1 | 10/2008 | Wagner et al. |
| 2008/0302839 A1 | 12/2008 | Murdoch et al. |
| 2008/0319362 A1 | 12/2008 | Joseph |
| 2009/0025115 A1 | 1/2009 | Duffy et al. |
| 2009/0030353 A1 | 1/2009 | Bonutti et al. |
| 2009/0030359 A1 | 1/2009 | Wikenheiser et al. |
| 2009/0062704 A1 | 3/2009 | Brown et al. |
| 2009/0082707 A1 | 3/2009 | Rumsey |
| 2009/0100649 A1 | 4/2009 | Bar et al. |
| 2009/0124948 A1 | 5/2009 | Ingimundarson et al. |
| 2009/0127308 A1 | 5/2009 | Mori et al. |
| 2009/0182253 A1 | 7/2009 | Grim et al. |
| 2009/0192425 A1* | 7/2009 | Garth ............ A61F 5/028 602/19 |
| 2009/0198166 A1 | 8/2009 | Shlomovitz |
| 2009/0275871 A1 | 11/2009 | Liu |
| 2009/0287128 A1 | 11/2009 | Ingimundarson et al. |
| 2010/0010568 A1 | 1/2010 | Brown |
| 2010/0037369 A1 | 2/2010 | Reichert |
| 2010/0139057 A1 | 6/2010 | Soderberg et al. |
| 2010/0204630 A1* | 8/2010 | Sandifer ............ A61F 5/026 602/19 |
| 2010/0205713 A1 | 8/2010 | Takamoto et al. |
| 2010/0217167 A1 | 8/2010 | Ingimundarson et al. |
| 2010/0228170 A1 | 9/2010 | Imai |
| 2010/0256717 A1 | 10/2010 | Brown |
| 2010/0268139 A1 | 10/2010 | Garth |
| 2010/0268141 A1 | 10/2010 | Bannister |
| 2010/0274364 A1 | 10/2010 | Pacanowsky et al. |
| 2010/0292622 A1 | 11/2010 | Weissleder et al. |
| 2010/0299959 A1 | 12/2010 | Hammerslag et al. |
| 2010/0318010 A1* | 12/2010 | Sandifer ............ A61F 5/026 602/19 |
| 2011/0000005 A1 | 1/2011 | Brown |
| 2011/0009793 A1 | 1/2011 | Lucero et al. |
| 2011/0046528 A1 | 2/2011 | Stevenson et al. |
| 2011/0082402 A1 | 4/2011 | Oddou et al. |
| 2011/0098618 A1 | 4/2011 | Fleming |
| 2011/0105971 A1 | 5/2011 | Ingimundarson et al. |
| 2011/0125183 A1* | 5/2011 | Lipshaw ............ A61F 13/085 606/201 |
| 2011/0137221 A1 | 6/2011 | Brown |
| 2011/0144551 A1 | 6/2011 | Johnson |
| 2011/0152737 A1 | 6/2011 | Burke et al. |

(56) References Cited

U.S. PATENT DOCUMENTS

| | | |
|---|---|---|
| 2011/0178448 A1 | 7/2011 | Einarsson |
| 2011/0184326 A1 | 7/2011 | Ingimundarson et al. |
| 2011/0266384 A1 | 11/2011 | Goodman et al. |
| 2012/0010547 A1 | 1/2012 | Hinds |
| 2012/0022420 A1 | 1/2012 | Sandifer et al. |
| 2012/0029404 A1 | 2/2012 | Weaver, II et al. |
| 2012/0078151 A1 | 3/2012 | Cropper |
| 2012/0197167 A1 | 8/2012 | Kruijsen et al. |
| 2012/0204381 A1 | 8/2012 | Ingimundarson et al. |
| 2012/0220910 A1 | 8/2012 | Gaylord et al. |
| 2012/0232450 A1 | 9/2012 | Garth et al. |
| 2012/0245502 A1 | 9/2012 | Garth et al. |
| 2012/0323154 A1 | 12/2012 | Ingimundarson et al. |
| 2013/0006158 A1 | 1/2013 | Ingimundarson et al. |
| 2013/0007946 A1 | 1/2013 | Brown |
| 2013/0012853 A1 | 1/2013 | Brown |
| 2013/0158457 A1 | 6/2013 | Garth et al. |
| 2013/0174326 A1 | 7/2013 | Takamoto et al. |
| 2013/0184628 A1 | 7/2013 | Ingimundarson et al. |
| 2013/0190670 A1 | 7/2013 | Von Zieglauer |
| 2013/0211302 A1 | 8/2013 | Brown |
| 2013/0237891 A1 | 9/2013 | Fryman et al. |
| 2013/0281901 A1 | 10/2013 | Ochoa |
| 2013/0298914 A1 | 11/2013 | Shibaya et al. |
| 2014/0081189 A1 | 3/2014 | Ingimundarson et al. |
| 2014/0116452 A1 | 5/2014 | Ingimundarson et al. |
| 2014/0135672 A1 | 5/2014 | Joseph et al. |
| 2014/0207040 A1 | 6/2014 | Ingimundarson et al. |
| 2014/0200121 A1 | 7/2014 | Von Hoffmann et al. |
| 2014/0207041 A1 | 7/2014 | Ingimundarson et al. |
| 2014/0336020 A1 | 11/2014 | Von Hoffmann et al. |
| 2016/0228279 A1 | 8/2016 | Modglin et al. |
| 2016/0250061 A1 | 9/2016 | Ingimundarson et al. |

FOREIGN PATENT DOCUMENTS

| | | |
|---|---|---|
| AU | 20 1028 68 51 A1 | 3/2012 |
| AU | 20 1028 68 51 A2 | 5/2012 |
| CA | 2 112 789 A1 | 8/1994 |
| CA | 2 114 387 A1 | 8/1994 |
| CA | 2 767 353 A1 | 1/2011 |
| CA | 2 772 296 A1 | 3/2011 |
| CH | 577 282 A5 | 7/1976 |
| CH | 612 076 A5 | 7/1979 |
| CH | 624 001 A5 | 7/1981 |
| CN | 1461190 A | 12/2003 |
| CN | 201101603 Y | 8/2008 |
| CN | 101444443 A | 6/2009 |
| CN | 101820783 A | 9/2010 |
| CN | 102470040 A | 5/2012 |
| DE | 38 22 113 A1 | 1/1990 |
| DE | 93 15 776 U1 | 2/1995 |
| DE | 295 03 552 U1 | 4/1995 |
| DE | 199 45 045 A1 | 3/2001 |
| DE | 20 2004 015 328 U1 | 2/2005 |
| DE | 20 2005 007 124 U1 | 6/2005 |
| DE | 20 2009 004 817 U1 | 9/2010 |
| EP | 0 393 380 B1 | 9/1992 |
| EP | 0 589 233 A1 | 3/1994 |
| EP | 0 614 624 A1 | 9/1994 |
| EP | 0 614 625 A1 | 9/1994 |
| EP | 0 589 232 B1 | 11/1995 |
| EP | 0 693 260 B1 | 9/1998 |
| EP | 0 651 954 B1 | 2/1999 |
| EP | 1016351 A1 | 7/2000 |
| EP | 1 236 412 A1 | 9/2002 |
| EP | 1 342 423 A1 | 9/2003 |
| EP | 1 588 678 A1 | 10/2005 |
| EP | 1 743 608 A2 | 1/2007 |
| EP | 1 985 264 A1 | 10/2008 |
| EP | 2 200 545 A1 | 6/2010 |
| EP | 2 451 412 A1 | 5/2012 |
| EP | 2 473 072 A1 | 7/2012 |
| FR | 2 952 807 A1 | 5/2011 |
| GB | 826 041 A | 12/1959 |
| JP | 3031760 U | 12/1996 |
| JP | H09-273582 A | 10/1997 |
| JP | H10-237708 A | 9/1998 |
| JP | 2000-290331 A | 10/2000 |
| JP | 2003-175063 A | 6/2003 |
| JP | 2004-016732 A | 1/2004 |
| JP | 2004-041666 A | 2/2004 |
| JP | 2007-291536 A | 11/2007 |
| JP | 3142546 U | 6/2008 |
| JP | 2009-082697 A | 4/2009 |
| JP | 2012-011550 A | 1/2012 |
| JP | 2013-503268 A | 1/2013 |
| JP | 2013-536010 A | 9/2013 |
| WO | 94/01496 A1 | 1/1994 |
| WO | 95/03720 A2 | 2/1995 |
| WO | 97/03581 A1 | 2/1997 |
| WO | 00/53045 A1 | 9/2000 |
| WO | 2004/110197 A2 | 12/2004 |
| WO | 2005/086752 A3 | 4/2005 |
| WO | 2005/086752 A2 | 9/2005 |
| WO | 2006/121413 A1 | 11/2006 |
| WO | 2007003148 A1 | 1/2007 |
| WO | 2009/017499 A1 | 2/2009 |
| WO | 2009/017949 A1 | 2/2009 |
| WO | 2009/052031 A1 | 4/2009 |
| WO | 2009/068503 A1 | 6/2009 |
| WO | 2011/005430 A1 | 1/2011 |
| WO | 2011/025675 A1 | 3/2011 |
| WO | 2011066323 A1 | 6/2011 |
| WO | 2012/029917 A1 | 3/2012 |
| WO | 2013-016670 A1 | 1/2013 |
| WO | 2016138215 A1 | 9/2016 |

OTHER PUBLICATIONS

Mehlman, Charles T. et al., "Hyphenated History: Knight-Taylor Spinal Olthosis"; American Journal of Orthopedics; Jun. 2000; pp. 479-483, vol. 29, Issue 6.

Bledsoe Products, "Philippon K.A.F. Positioning Kit". Http:// bledsoebrace.com/products/kaf.asp [retrieved from the internet May 10, 2012].

Sato, Ena et al., "Effect of the WISH-type hip brace on functional mobility in patients with osteoarthritis of the hip: evaluation using the timed UP & GO Test", Prosthetics and Orthotics International 2012 36:25 originally published online Nov. 17, 2011, http://poi.sagepub.com/content/36/125 [retrieved from internet on Jan. 22, 2014].

International Search Report from PCT Application No. PCT/US2018/049969, dated Nov. 16, 2018.

Pamphlet—"Bledsoe Phillippon K.A.F. Positioning Kit, Application Instructions (CP020205 Rev B 04/07), New Hip Arthroscopy Padding and Positioning Kit", Council Directive 93/42/EEC of Jun. 14, 1993 concerning Medical Devices, 2 pages.

Mehlman, Charles T. et al., "Hyphenated History: Knight-Taylor Spinal Orthosis"; American Journal of Orthopedics Jun. 2000; pp. 479-483, vol. 29, Issue 6.

Pamphlet—"Bledsoe Phillippon K.A.F. Positioning Kit", Bledsoe Brace Systems, Medical Technology Inc., 2004, 2 pages.

Posture Control Brace. Soft Form, Orthopaedic by Design, FLA Orthopedics, Inc, 1 page; 2004. http://www.flaorthopedics.com.

Michael Pfiefer, MD et al., "Effects of a New Spinal Orthosis on Posture, Trunk Strength, and Quality of Life in Women with Postmenopausal Osteoporosis—a Randomized Trial", American Journal of Physical Medicine & Rehabilitation, vol. 83, No. 3, Mar. 2004, USA, pp. 177-186.

Scoliosis Specialists. About the SpineCor Brace; 2006-2012; http://www.scoliosisspecialists.com/aboutspinecorbrace.html. Retrieved from Internet on Aug. 1, 2013.

Hsu et al., "Principles and Components of Spinal Orthoses", AAOS Atlas of Orthoses and Assistive Devices, 4th Ed., Chapter 7,2008, pp. 89-111.

Bledsoe Products, "Philippon K.A.F. Positioning Kit". Http:// bledsoebrace.com/products/kaf.asp [retrieved from the nternet May 10, 2012].

(56) References Cited

OTHER PUBLICATIONS

Spinomed Brochure—Spinal Orthosis for Vertebral Extension in Osteoporosis; Stellar Orthotics and Prosthetics Group, 2 pages, retrieved from Internet Sep. 23, 2013. http://www.stellaroandp.com/spotlight.html.
Sato, Ena et al., "Effect of the WISH-type hip brace on functional mobility in patients with osteoarthritis of the hip evaluation using the timed UP & GO Test", Prosthetics and Orthotics International 2012 36:25 originally published inline Nov. 17, 2011, http://poi.sagepub.eom/content/36/125 [retrieved from internet on Jan. 22, 2014].
Silosheath Brochure, Soft Socket Gel Liner, 4 pages, 1994.

\* cited by examiner

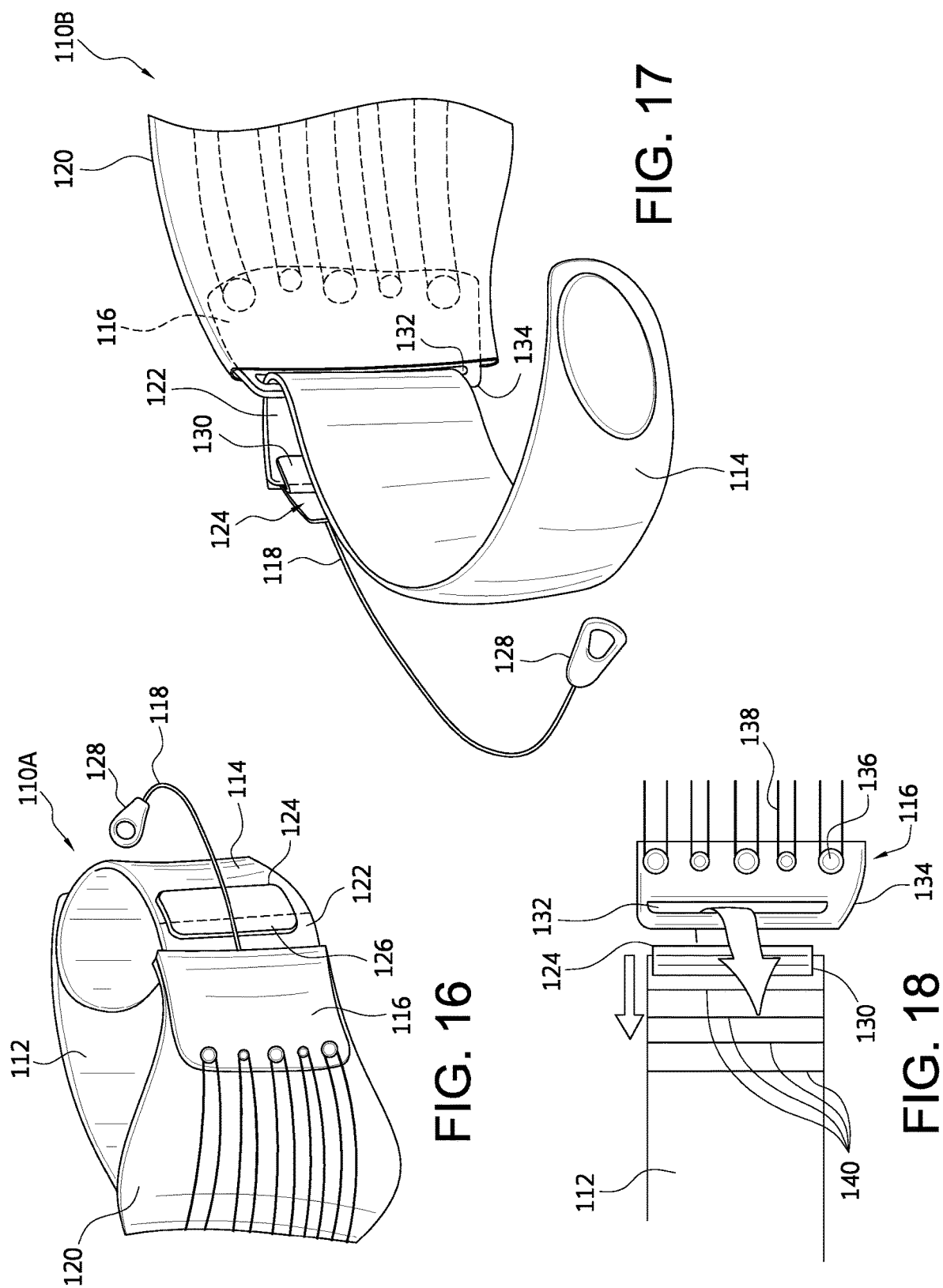

US 11,484,428 B2

PANEL ATTACHMENT AND CIRCUMFERENCE ADJUSTMENT SYSTEMS FOR AN ORTHOPEDIC DEVICE

FIELD OF THE DISCLOSURE

The disclosure relates to a panel and attachment system for an orthopedic device, and more particularly to a rigid or semi-rigid panel and a system for attaching the panel to a spinal orthosis and a belt circumference system for reducing a length of belt members.

BACKGROUND

A spinal orthosis or lumbar belt is an orthopedic device designed for pain relief, protecting injured ligaments or muscles and post-surgical immobilization. A spinal orthosis is arranged to relieve pressure over the spinous processes while applying an even pressure to the paraspinal musculature to ensure comfortable and effective healing. Typical indications for lumbar supports include spinal stenosis, herniated discs, post-surgical stabilization, stable and non-displaced spinal fractures, spondylolithesis, spondylolysis, and degenerative spinal pathologies.

In a known spinal orthosis in FIGS. 1-3, such as the exemplary spinal orthosis described in U.S. Pat. No. 8,172,779, granted on May 8, 2012 and incorporated by reference, the spinal orthosis has outer and inner sides configurations 10A, 10B, with the inner side arranged to be adjacent the wearer's back. The orthosis has first and second belts 12, 14, and a compression system 16 adapted to exert pressure onto the lumbar region of a wearer's back. The compression system 16 includes tightening elements or drawstrings 18 that permit the wearer to adjust pressure over the back and a cover 20 extending over the compression system 16.

A flexible or semi-rigid back plate 22 extends over at least part of the compression system 16, and is arranged to be adjacent the back. The back plate 22 includes a posterior attachment system 24 for a rigid posterior panel 26, which includes a single hook and loop system connected at a single attachment point or flap 25 centered on the back plate 22. An anterior panel may be attached to the spinal orthosis at an anterior attachment system 29 on one of the belts.

The posterior panel provides enhanced support to satisfy the immobilization needs of the wearer. Since the immobilization needs may change over treatment, it is desirable that the posterior panel is removable if additional support is required or the support by the posterior panel is excessive such that no posterior panel is required. Posterior panels may have different shapes depending on the type and level of required support, and the size of the wearer should it change over course of treatment. In the depicted embodiment of FIG. 3, the posterior panel has lateral supports 27.

As depicted in FIG. 3, the posterior panel 26 is substantially larger than the back plate 22, and is anatomically shaped for hugging the contours of the back. The anatomically shaped panel of this example has approximately 15 degrees of lordotic curve built into the contour of the panel. This allows for the panel and the spinal orthosis to apply a three-point pressure system creating an extension moment to the spine, with two forces in the front, and one force in the center of the back.

In the exemplary prior art spinal orthosis, it has been found it is difficult to maintain rotational control of the posterior panel relative to the back plate with the known attachment system. The adjustment system does not allow for visible adjustment of the connection of the posterior panel, and it is easy to poorly adjust and ineffectively secure the posterior panel to the spinal orthosis.

Known posterior panels are ill-suited for post-operative use, particular when they are not customized for wearers. Known panels lack means to avoid incision sites on wearers that result from back operations.

SUMMARY

Under embodiments of the invention, posterior panels are arranged with a flat spinal curvature to create a reverse three-point pressure system over the prior art posterior panels that create a flexion moment to the spine. This reverse three-point pressure system is provided to relieve pressure on the posterior side of the vertebrae beneficial for certain indications such as spinal stenosis.

The embodiments are flexible in the sense that prior to placement against a wearer's back, the panel can flex in flexion or extension around the spinal area and laterally around a lateral support if provided on the panel. The panels become semi-rigid or rigid when the panel is coupled to a spinal orthosis, and placed against the lumbar region of the wearer. The compression system draws the panel firmly against the back so it conforms to the wearer's anatomy, and the panel becomes semi-rigid or rigid against the wearer's back due to the pressure exerted by the compression system and due to a cylindrical effect that occurs because of the panel being urged to conform to the anatomy of the wearer.

In a variation of the embodiment, an opening is provided around the spinal area of the posterior panels to ensure there is no risk of the panel coming into contact with a wearer's incision site or otherwise sensitive area along the spinal area.

In another variation of the embodiment, the posterior panel is provided with lateral supports with peripheral cut-out sections between the lateral supports and a main body portion. The cut-outs have the benefit of creating flexibility for the panel during compression and rigidifying the panel against the wearer to accommodate different body shapes.

An attachment system may be on a cover of a back plate that permits more user-friendly securement and rotational control of the posterior panel on the spinal orthosis. According to an embodiment of the attachment system, the cover of the back panel includes a pair of vertical slits and corresponding openings that allow for opposed straps secured to the posterior panel to couple therewith. This arrangement permits full visibility of the straps as they secure to the cover, and the provision of two attachment points inhibits rotation of the posterior panel relative to the back panel and improves the strength of the connection.

The attachment system may be similarly employed for attaching an anterior panel to a spinal orthosis by providing the attachment system along one of the belt members, and aligning the same so it centrally faces the abdomen of the wearer.

In another embodiment, the orthopedic device includes a belt circumference adjustment system permitting a reduction in the circumference of the spinal orthosis. The spinal orthosis includes a back unit, and first and second belt members connected to the back panel and having first and second end portions. Each of the first and second belt members is arranged for being reduced in length at the first and second end portions. The first and second belt members are formed a belt having a circumference with the back unit. Each of the belt members may include a belt panel having opposed sections arranged for coupling to one of the first and second end portions of at least one of the first and second belt members, and a leading section arranged for coupling one of the first and second belt members.

The back unit may include first and second tabs each defining an elongate slot through which the first and second end portions extend. The leading section of the at least one belt panel secures to a surface of a respective one of the belt members onto which the at least one panel is secured. The at least one belt panel may be extended through the elongate slot while carried by a respective one of the belt members.

In another variation, the belt panel may be secured onto a first end portion of the first belt member, and the second end portion of the first belt member securing to the back unit.

BRIEF DESCRIPTION OF THE DRAWINGS

These and other features, aspects, and advantages of the present invention will become better understood regarding the following description, appended claims, and accompanying drawings.

FIG. 16 is a schematic view showing another embodiment of a spinal orthosis.

FIG. 17 is a detailed schematic view showing the spinal orthosis of FIG. 16.

FIG. 18 is a detailed schematic view showing attachment of a belt segment of the spinal orthosis of FIG. 16.

Figure 1:
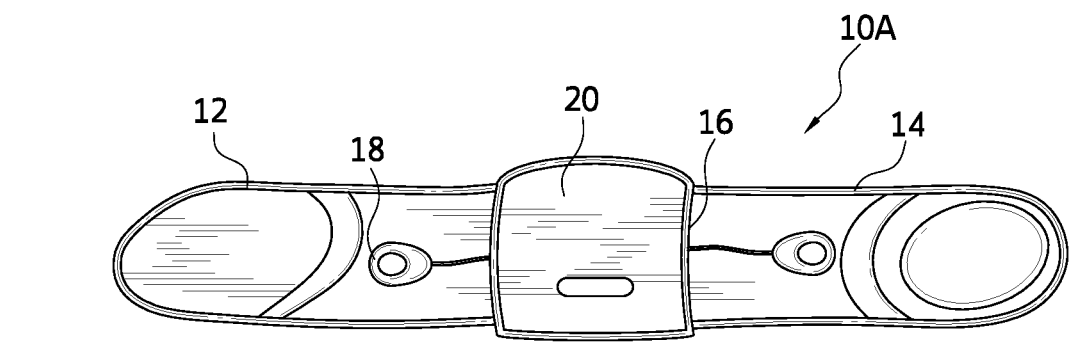
FIG. 1 shows an outer side of a prior art spinal orthosis.
Figure 2:
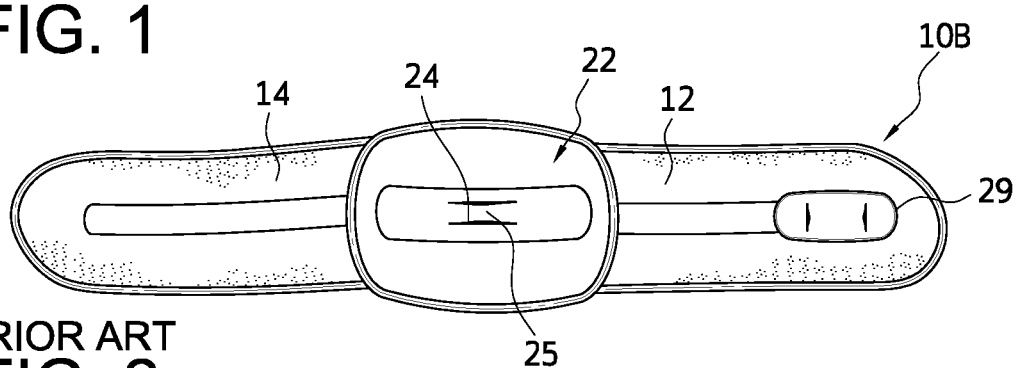
FIG. 2 shows an inner side of the prior art spinal orthosis of FIG. 1.
Figure 3:
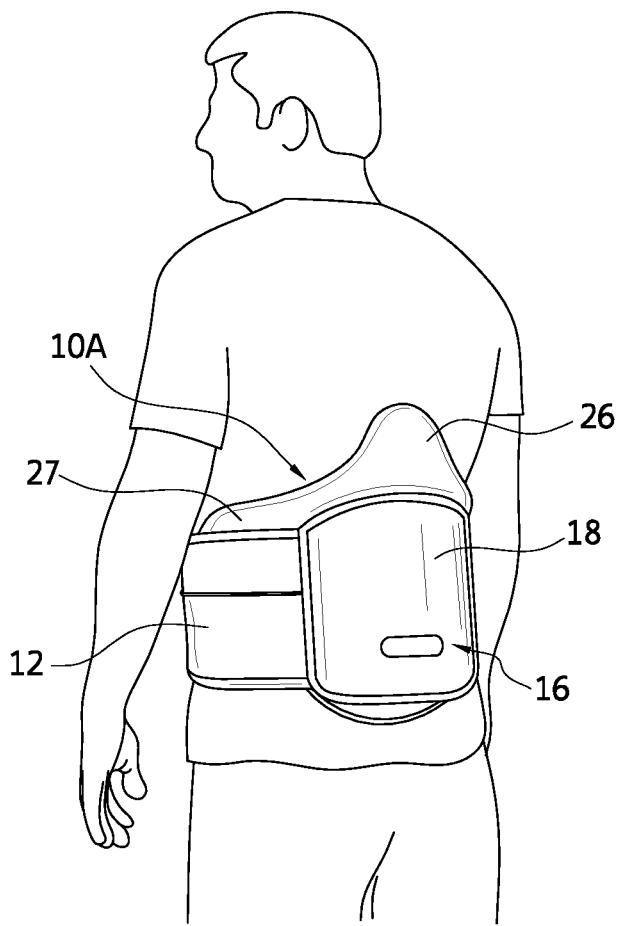
FIG. 3 is a perspective view of the prior art spinal orthosis of FIG. 1 having a posterior panel and placed on a wearer.

The drawing figures are not drawn to scale, but instead are drawn to provide a better understanding of the components, and are not intended to be limiting in scope, but rather to provide exemplary illustrations.

DETAILED DESCRIPTION OF VARIOUS EMBODIMENTS

A. Overview

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that, unless a term is expressly defined in this disclosure to possess a described meaning, there is no intent to limit the meaning of such term, either expressly or indirectly, beyond its plain or ordinary meaning.

The panel embodiments described are configured for use as posterior panels for placement against the back of a wearer. It should be remembered, however, that the same concepts and methods described may be similarly used for anterior panels adapted for a spinal orthosis.

B. Embodiments of the Panel and Attachment System

Figure 4:
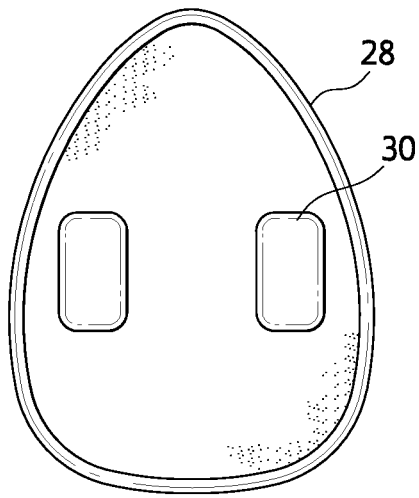
FIG. 4 shows an embodiment of a posterior panel.
Figure 5:
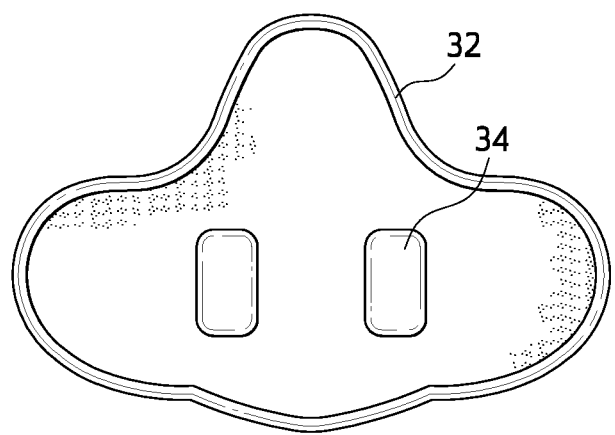
FIG. 5 shows another posterior panel embodiment.
Figure 6:
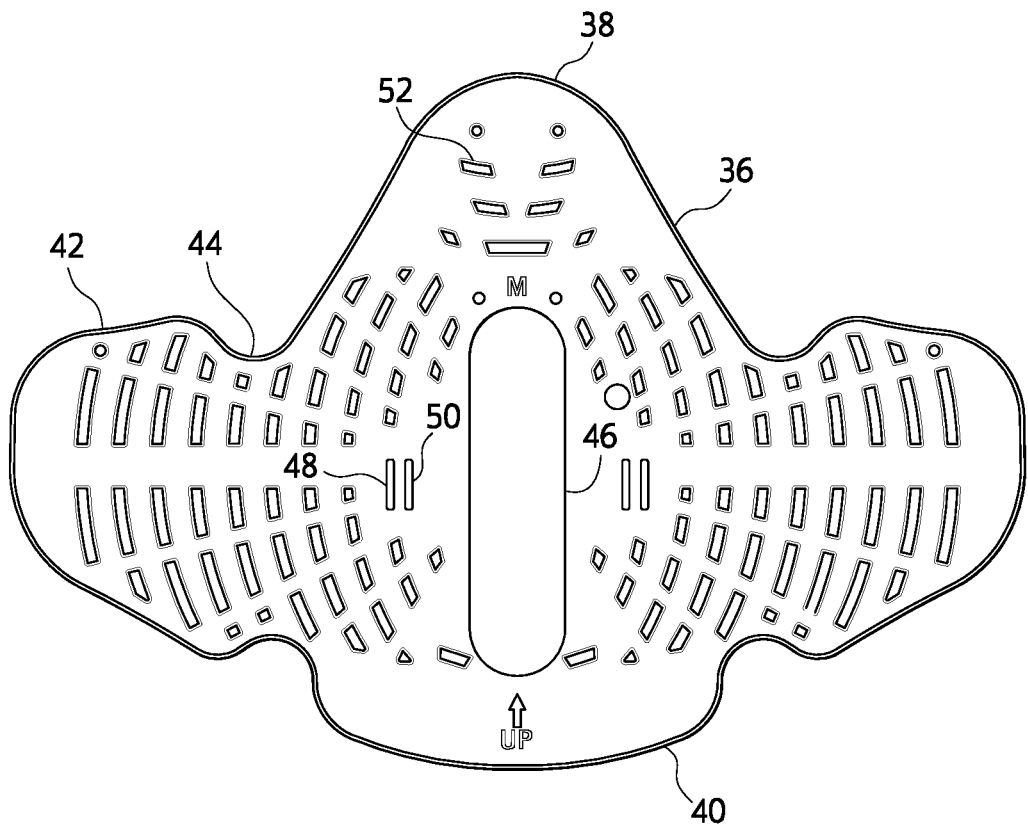
FIG. 6 shows a posterior panel embodiment having lateral supports.

In referring to FIGS. 4-6, different posterior panels may be used with a spinal orthosis. Each of these panels is preferably flexible in the sense that prior to placement against a wearer's back, the panel can flex in flexion or extension around the spinal area and laterally around a lateral support if provided on the panel. The panels become semi-rigid or rigid when the panel is coupled to a spinal orthosis, and placed against the lumbar region of the wearer. The compression system draws the panel firmly against the back so it conforms to the wearer's anatomy, and the panel become semi-rigid or rigid against the wearer's back due to the pressure exerted by the compression system and due to a cylindrical effect that occurs because of the panel being urged to conform to the anatomy of the wearer. Alternatively, the panel may be wholly rigid or fully flexible before, during and after use with the compression system.

FIG. 4 shows a flat flexible non-lateral posterior panel 28, having at least a pair of attachment strips 30. FIG. 5 shows a flat-flexible lateral posterior panel 32 having attachment strips and lateral supports. As with the panels described, each panel may include a padded cover comprising foam, textile or a combination. An example of a cover 72 is in part in reference to the schematic views of FIGS. 11-14.

FIG. 6 illustrates a posterior panel 36 having a top portion 38 tapering from a main body portion 52, a bottom portion 40 having a greater width than the top portion, and lateral supports 42 extending laterally from the main body portion 52. The panel 36 defines notches 44 including upper and lower portions and located between the lateral supports 42 and the main body portion 52. The notches 44 facilitate bending of the panel about the torso of the wearer without compromising eventual rigidity of the panel 36 when used in combination with the compression system.

The panel 36 defines an elongate central opening 46 provided around the spinal area of the panel 36 to ensure there is no risk of the panel coming into contact with a wearer's incision site or otherwise sensitive area along the spinal area. The panel also defines a plurality of apertures in part to improve ventilation of the panel when worn by the wearer. The apertures may also be improved bending of the panel about the anatomy of the wearer. The apertures are arranged in combination with the lateral supports in an arcuate configuration that allows the panel to bend in an anatomically friendly manner. The panel 36 also defines at least two vertically arranged slits 48, 50 arranged for receiving a strap.

Figure 7:
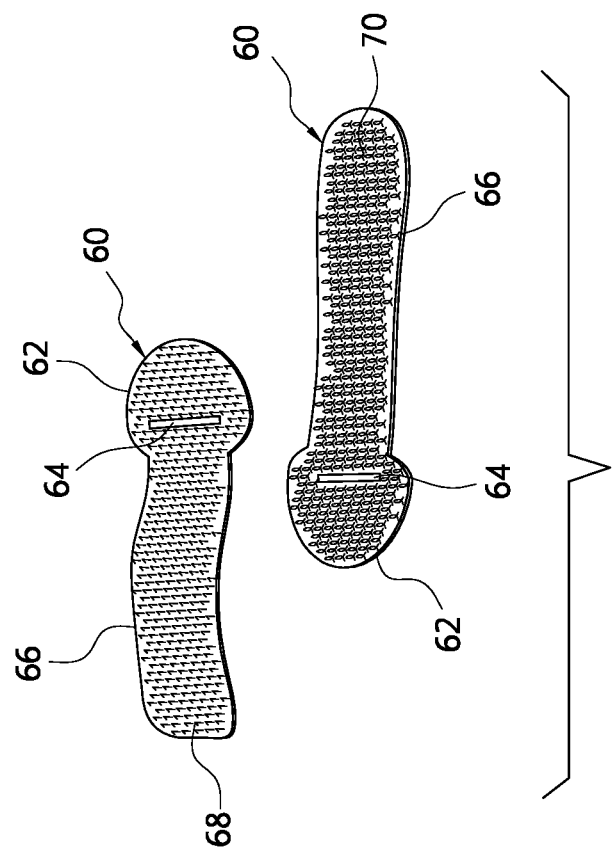
FIG. 7 illustrates outer and inner sides of a strap for an attachment system.

The strap may be configured as shown in the embodiment of FIG. 7. In this embodiment, the strap 60 has a hook surface 68 and a hook-receivable surface 70. The strap 60 defines a base portion 62 have a greater width than the slits 48, 50 to prevent the base portion 62 from passing through the slits. The strap further defines an elongate arm 66, which is extended through a passageway 64 formed between the base portion 62 and the arm 66.

Figure 8:
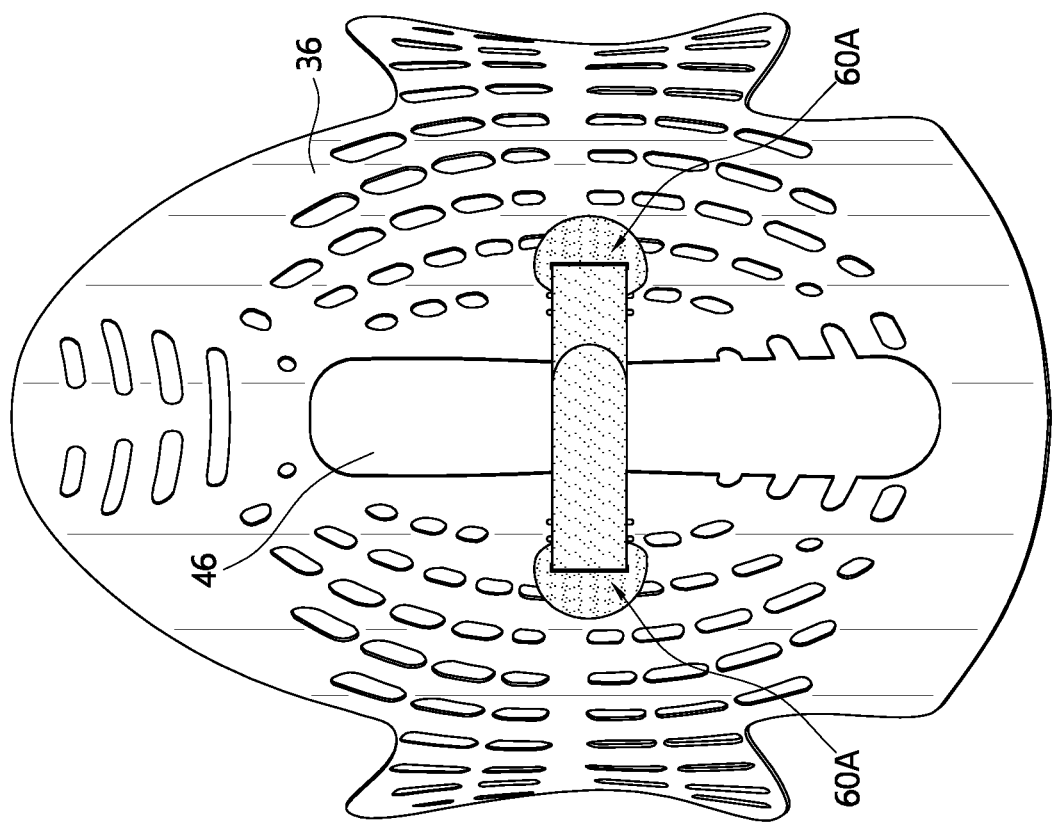
FIG. 8 shows the posterior panel of FIG. 6 having the straps in FIG. 7.

As depicted in FIG. 8, the arm 66 is adapted to extend through a first slit, through the passageway 64, and a second slit to secure the strap to the panel, with the hook surface 68 securable to the hook-receivable surface 70.

Figure 9:
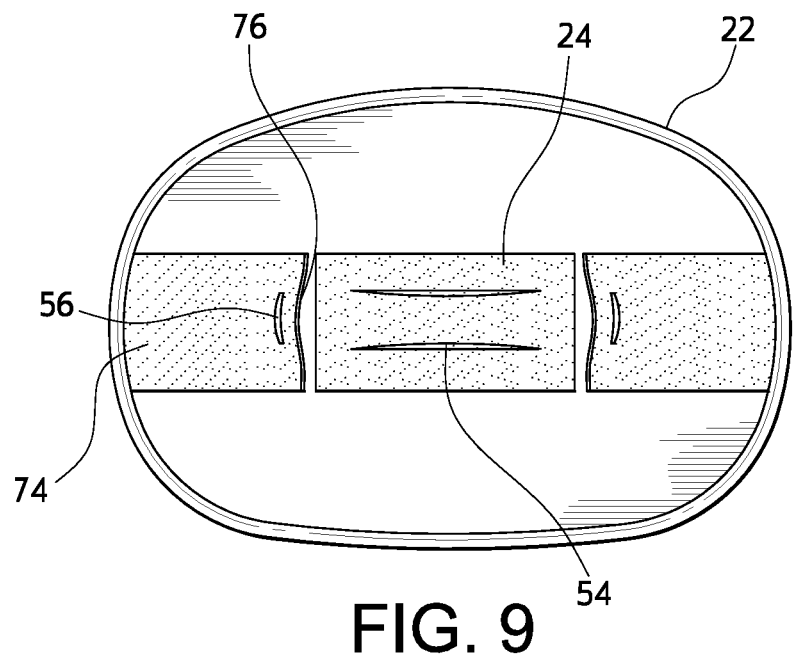
FIG. 9 shows a back plate having a cover including part of an attachment system.

In reference to FIG. 9, the cover of the back plate 22 includes the attachment system 24. The attachment system 24 includes a hook receivable central segment including pair of laterally extending slits 54 for receiving a single prior art strap used to attach the posterior panel to the spinal orthosis. The attachment system 24 also includes a pair of vertically extending slits 56 and a laterally extending hook-receivable segments 74 spaced apart from one another by the central segment and having openings 76 which permit a strap to extend to the slits 56. The laterally extending segments 74 are spaced apart to accommodate panel embodiments having an elongate vertical opening as in the embodiment of FIG. 6.

Figure 10:
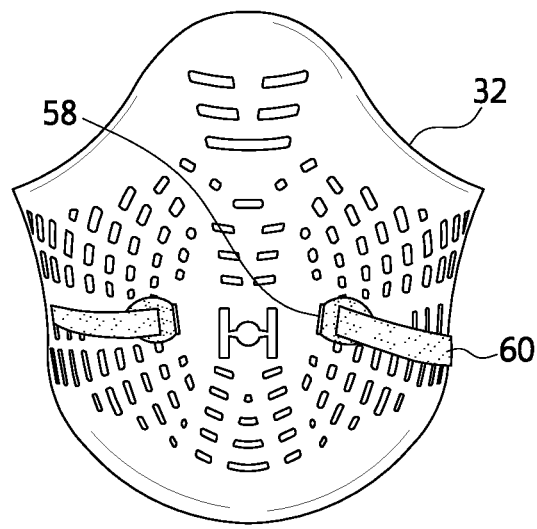
FIG. 10 shows the posterior panel of FIG. 5 including the straps in FIG. 7.
Figure 11:
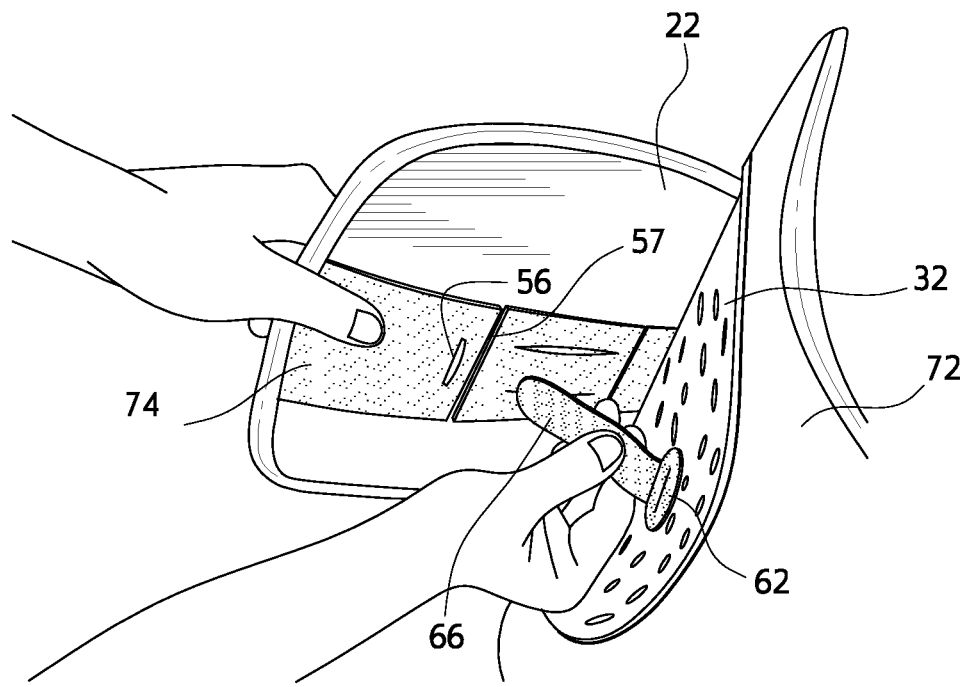
FIG. 11 is a schematic view showing a step of attaching the posterior panel to the back plate.

Turning to FIG. 10, the panel embodiment of FIG. 5 includes the straps 60 of FIG. 7 extending through slits 58, 60.

Figure 12:
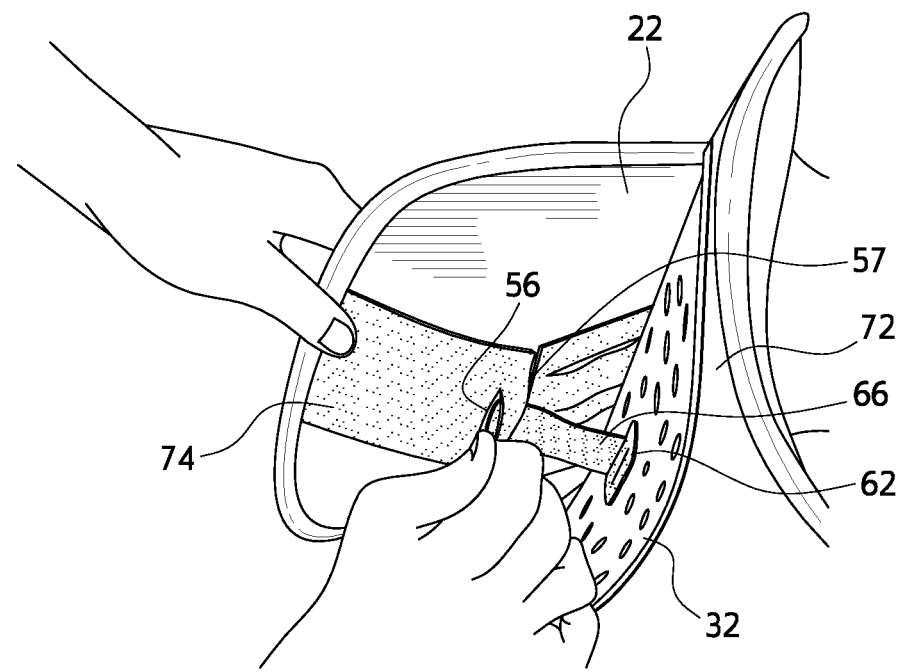
FIG. 12 is another schematic view showing a step of attaching the posterior panel to the back plate.
Figure 13:
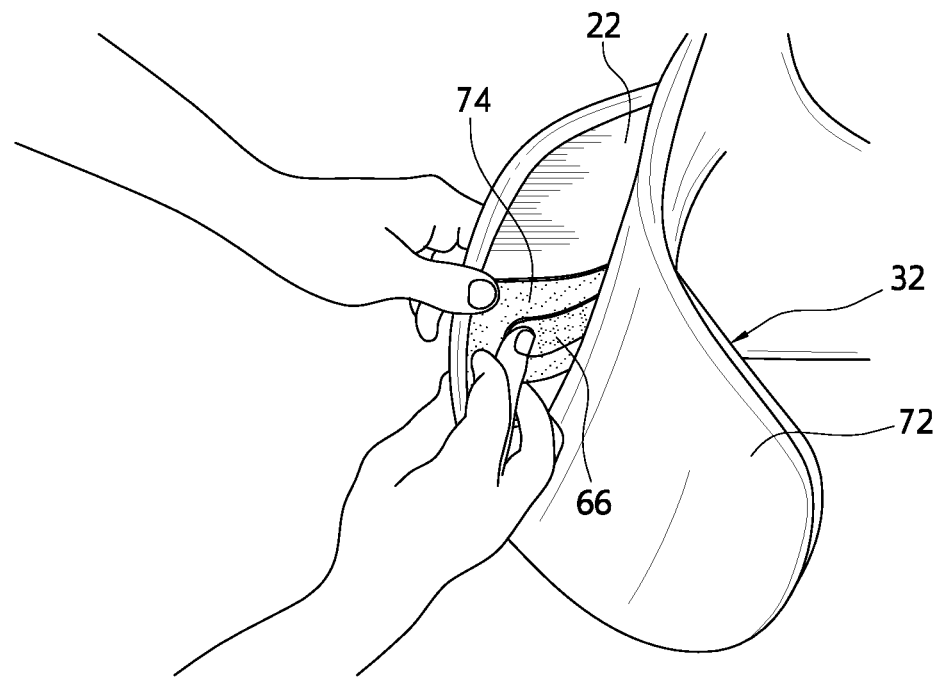
FIG. 13 is yet another schematic view showing a step of attaching the posterior panel to the back plate.

FIGS. 11-14 depict a method for attaching the posterior panel of FIG. 10 including a cover 72 and the straps 60 to the attachment system 24 of the back plate 22 of FIG. 9. According to the first step in FIG. 11, the arm 66 of the strap is threaded through the opening 57 of the laterally extending segment 74. Next, FIG. 12 depicts the arm 66 as pulled through the vertically extending slit 56. The arm 66 is tensioned in view of the base 62 serving as an anchor and the hook surface of the arm 66 is tightly secured against the laterally extending segment 74 has a hook-receivable surface to engage the hook and hook-receivable material together.

Figure 14:
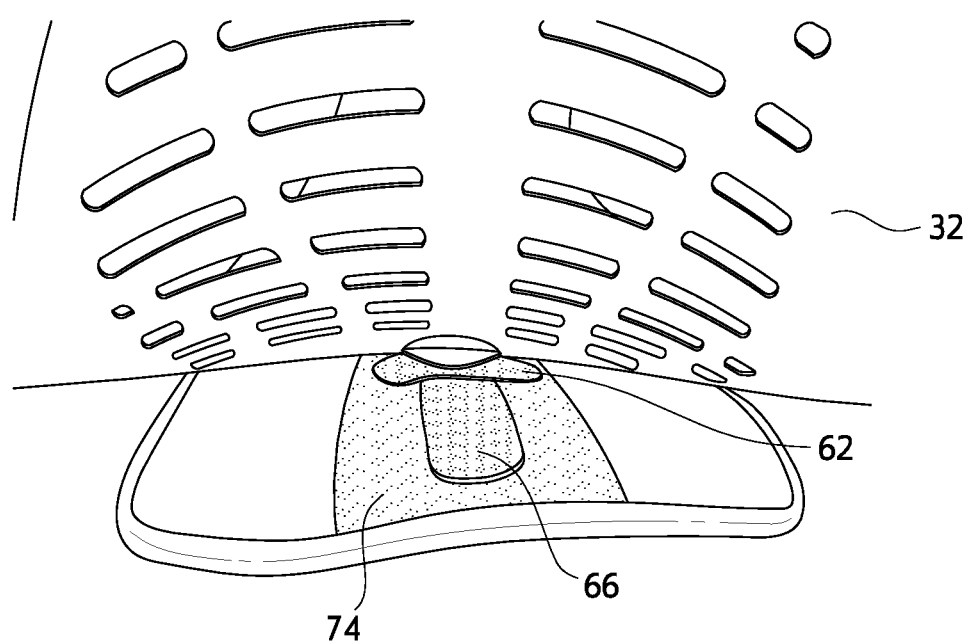
FIG. 14 is a schematic view showing the visibility of the attachment of the strap to the cover.

FIG. 14 shows the hook surface of the base 62 as likewise extending along the laterally extending surface 74 and likewise preventing slippage of the strap 60 from the panel. In view of the laterally extending nature of the arm, the clinician securing the panel to the back plate can view how the arm is secured to the back plate that assures the strap is properly secured and aligned. In view of the straps being on the sides, an easier work environment is provided for the clinician when the spinal orthosis is assembled for a wearer. The panel and back plate are rotated 180 degrees and the strap on the opposite side is secured as in FIGS. 11-14.

Figure 15:
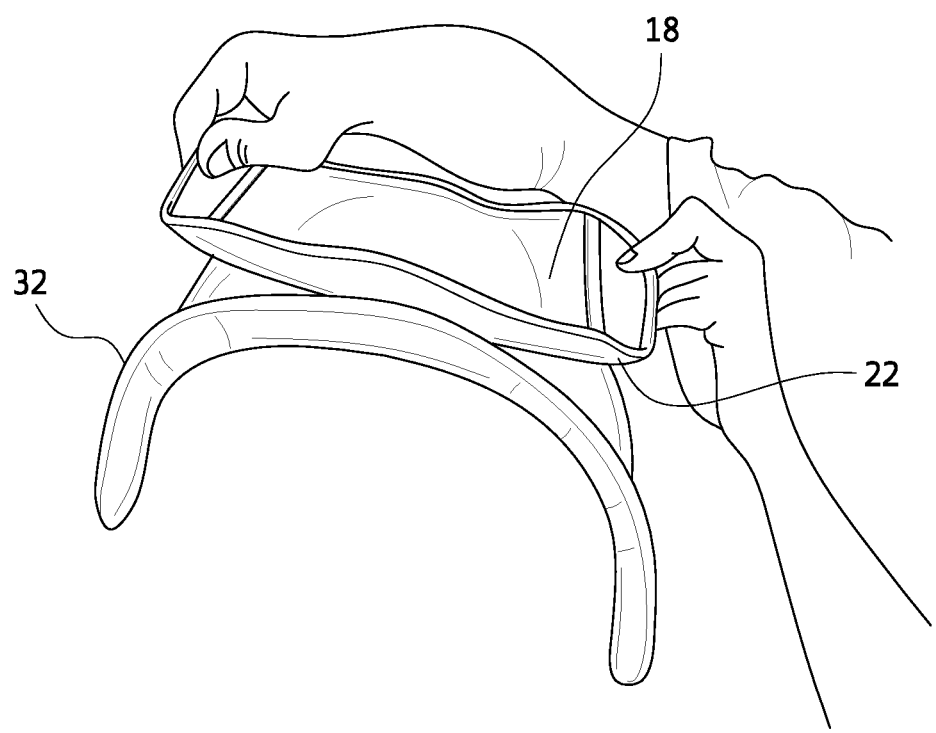
FIG. 15 is a schematic view showing the attachment of the back plate to the posterior panel with rotational control.

FIG. 15 depicts how the two straps securing the posterior panel 32 to the back plate 22 prevent rotation of the panel relative to the plate. Any movement of the posterior panel is mitigated or eliminated in view of the attachment system. The hook and loop connection only works in shear since the strap base creates an anchor point to retain the strap in a lateral position and has strength to retain the strap to the posterior panel.

C. Embodiments of the Belt Member Length Adjustment System

Turning to the embodiment of FIGS. 16-18, the spinal orthosis 110 has a belt member length adjustment system enable a reduction in circumference of a belt circumference of the spinal orthosis. The belt circumference includes first and second belt segments 112, 114 arranged to be connected to one another on the anterior of the wearer, and are connected on the posterior side by a back unit, preferably including a compression system 116, to form a belt circumference.

Elongate tensioning elements 118 extend from first and second sides of the spinal orthosis, coupling to the compression system 116 and secured over the anterior of the wearer on the first and second belt segments 112, 114. A handle 128 is secured to an end of the tensioning elements 118 and is securable to the first and second belt segments. A cover 120 is provided to extend over the compression system 116.

Each of the belt segments 112, 114 is reducible in length preferably at its posterior end, and the posterior end is securable to the compression system 116 after the belt segment 112, 114 is reduced in length.

The reduced end of the belt segment 112, 114 is attached to the compression system 116 by looping a segment 122 of the belt segment 112, 114 through a slot 132 formed on a plate 134 of the compression system 116. The plate 134 is modified over the plate in U.S. Pat. No. 8,172,779, and carries a plurality of reduction elements 136, such as pulleys or posts, and at least one cable 138. The belt member 112, 114 may be reduced in length along a plurality of locations 140. The locations 140 may be identified on the belt member 112, 114 by indicia defining different lengths.

The segment 122 attaches to an outer surface of the belt member 112, 114 by a clip or belt panel having two opposed clamping sections 126, 130 clamped onto opposed sides of the segment 122, and a leading section 124 extending from the clamping sections 126, 130 and removably securing to the outer surface of the belt member 112, 114. The clamping sections 126, 130 preferably engage the segment 122 by fasteners, such as by a hook and loop wherein the clamping sections 126, 130 include hook material and the outer and an inner surface of the belt segment 112, 114 includes a loop material that is hook receivable. The leading section 128 likewise may include hook material and secure to the hook receivable surface of the belt members 112, 114.

The segment 122 may be looped through the slot 132 in either orientation, so the leading section 128 secures over the outer or inner surfaces of the belt member 112, 114.

Figure 19:
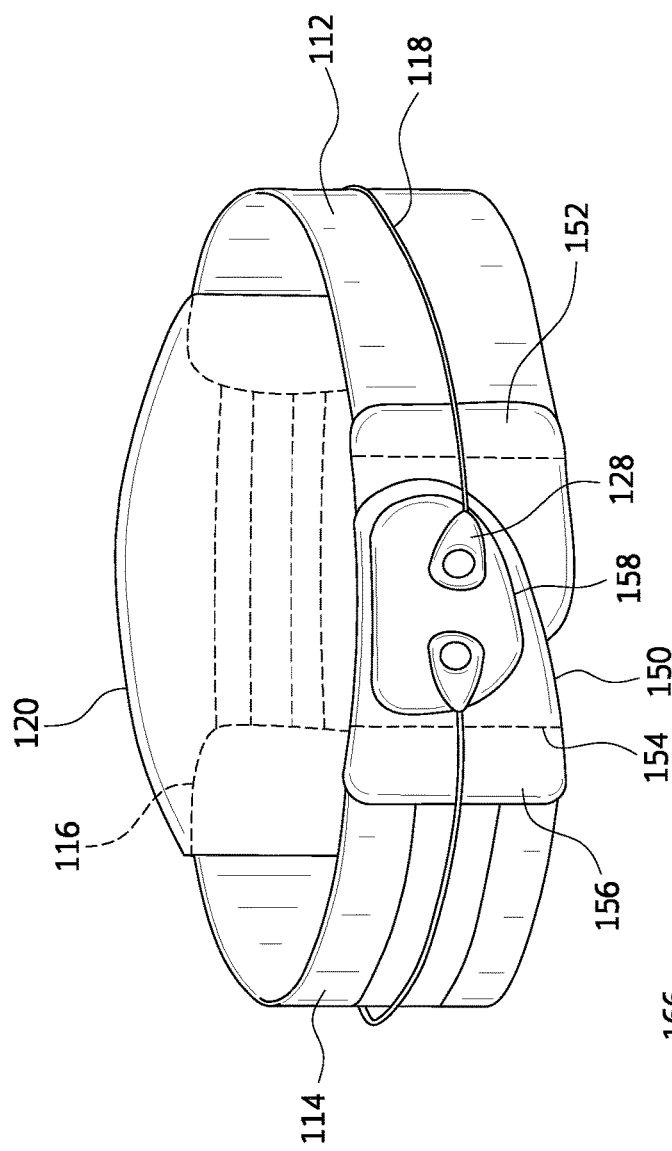
FIG. 19 is a schematic view showing another embodiment of a spinal orthosis.
Figure 21:
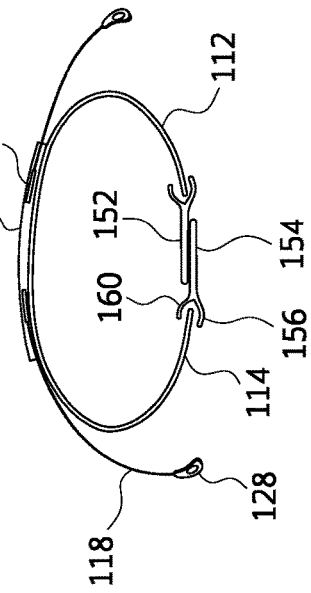
FIG. 21 is a plan view showing the spinal orthosis of FIG. 19.
Figure 20:
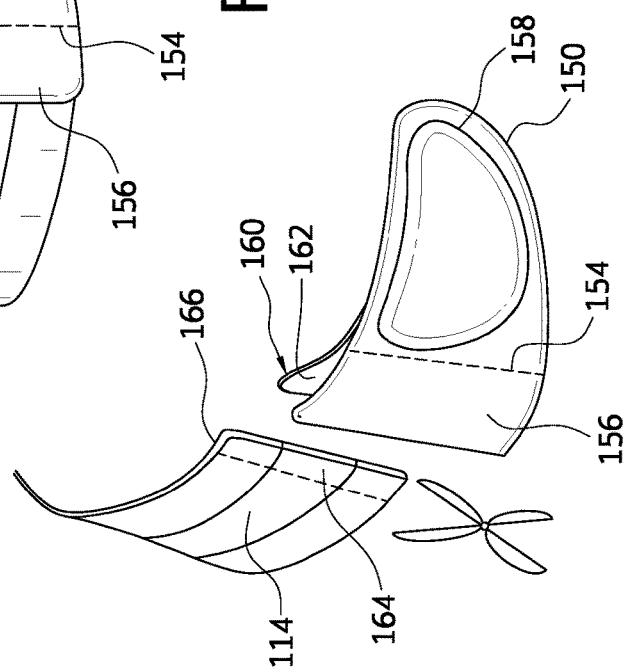
FIG. 20 is a perspective view of size adjustment of a belt segment of the spinal orthosis of FIG. 19.

FIGS. 19-21 illustrate another embodiment including a belt member length adjustment system wherein the spinal orthosis includes belt panels 150, 152 removably securable to the belt members 112, 114. In this embodiment, rather than reduce the length of the belt member 112, 114 at the posterior end, the belt member is reduced in length at the anterior end 164.

The belt panels 150, 152 have clamping sections 156, 160 secured to opposed sides of the belt members 112, 114 and terminate at a stitched or termination point 154 leaving a forward end 158 of the front panels 150, 152 to secure on the opposing belt panel carried by an opposing belt member. The clamping sections 156, 160 may include a fastener material 162 secured to the surface of the belt members 112, 114. A segment 166 of the belt member 112, 114 may be reduced at the anterior end 164 and removed by cutting or other appropriate means. The front panels 150, 152 may include padding or may be reinforced with rigid, semi-rigid or flexible shells.

While the foregoing embodiments have been described and shown, alternatives and modifications of these embodiments, such as those suggested by others may be made to fall within the scope of the invention. While the orthosis has been described in combination with a spinal orthosis, it will be understood that the principles described may be extended to other types of orthopedic and prosthetic devices.

The invention claimed is:

1. A spinal orthosis, comprising:
   a back unit;
   first and second belt members having first and second end portions, the second end portions removably securing to the back unit, each of the first and second belt members arranged for being reduced in length from the second end portions such that the second end portions are arranged with a leading section securable to a surface of the respective first and second belt members, the first and second belt members arranged to form a belt having a circumference with the back unit by the first end portions removably securing to one another;
   wherein the first end portion of the first and second belt members corresponds to an anterior side of the spinal orthosis and the first and second belt members are reducible in length of the respective one of the first and second belt members defined as a length between an anterior end of the first end portion to the second end portion secured to back panel;
   first and second belt panels each having an anterior clamping section arranged to secure to the anterior end of the first and second belt members, respectively, the first and second belt panels being arranged to secure to one another, each anterior clamping section having fastener material located along an interior surface thereof securable to at least one side of the first and second belt panels, the anterior clamping section being removable from both the first and second belt panels;
   the first and second belt panels each having a front panel forming first and second front sections separated by a stitched point, and a rear panel forming first and second rear sections separated by the stitched point, the second front section and second rear section bifurcate from the first front section and the first rear section at the stitched point, the first front section and the first rear section forming a forward end, the rear panel of the first belt panel arranged to secure to the front panel of the second belt panel.

2. The spinal orthosis of claim 1, wherein the back unit includes first and second plates defining first and second slots, respectively, such that the first and second belt members secure to the back plate via the first and second slots, respectively.

3. The spinal orthosis of claim 2, wherein the first and second plates each carry a plurality of reduction elements connected to one another by at least one cable.

4. The spinal orthosis of claim 3, wherein first and second elongate tensioning elements extend from first and second sides of the first and second plates, the first and second elongate tensioning elements including the at least one cable, each of the first and second elongate tensioning elements including a handle secured to a first end of the first and second elongate tensioning element and securable to the front panel of the first and second belt panels.

5. The spinal orthosis of claim 1, wherein the first and second belt members define a plurality of predetermined locations at the second end portions for defining different sizes of the belt members.

6. The spinal orthosis of claim 5, wherein the plurality predetermined locations are denoted by indicia representing different lengths of the first and second belt members.

7. The spinal orthosis of claim 1, further comprising a posterior plate being flexible and anatomically shaped to correspond to a lumbar region of a human back, the back plate attachable to the back unit.

8. The spinal orthosis of claim 1, wherein the first end portions of the first and second belt members have a geometric shape arranged to removably and repeatedly secure with one another.

9. The spinal orthosis of claim 1, wherein the back unit includes a compression system covered by a cover.

10. The spinal orthosis of claim 1, further comprises a posterior panel having a flexible configuration, and covered with a padded cover having a combination of foam and textile.

* * * * *